United States Patent
Engelbart et al.

(10) Patent No.: US 7,978,328 B2
(45) Date of Patent: Jul. 12, 2011

(54) VISION INSPECTION SYSTEM DEVICE AND METHOD

(75) Inventors: Roger W. Engelbart, St. Louis, MO (US); Reed Hannebaum, Belleville, IL (US); Tim Pollock, Ballwin, MO (US)

(73) Assignee: The Boeing Company, Chicago, IL (US)

( * ) Notice: Subject to any disclaimer, the term of this patent is extended or adjusted under 35 U.S.C. 154(b) by 515 days.

(21) Appl. No.: 12/107,579

(22) Filed: Apr. 22, 2008

(65) Prior Publication Data
US 2008/0259325 A1      Oct. 23, 2008

Related U.S. Application Data

(63) Continuation-in-part of application No. 11/390,244, filed on Mar. 28, 2006, now Pat. No. 7,362,437.

(51) Int. Cl.
*G01N 21/00* (2006.01)
(52) U.S. Cl. .............. 356/430; 356/237.1; 356/237.2
(58) Field of Classification Search .......... 356/430–435, 356/237.1–237.5
See application file for complete search history.

(56) References Cited

U.S. PATENT DOCUMENTS

| 7,039,485 B2 * | 5/2006 | Engelbart et al. ......... 700/110 |
| 7,362,437 B2 | 4/2008 | Engelbart et al. |
| 2004/0095586 A1 | 5/2004 | Stylios |
| 2005/0203657 A1 | 9/2005 | Engelbart et al. |
| 2007/0097359 A1 | 5/2007 | Engelbart et al. |

FOREIGN PATENT DOCUMENTS

| JP | 07071931 | 3/1995 |
| JP | 07229708 | 8/1995 |
| JP | 09321498 | 12/1997 |
| JP | 2003337012 | 11/2003 |

* cited by examiner

*Primary Examiner* — Michael P Stafira

(57) ABSTRACT

A course material that is applied to a substrate during fabrication of a composite item is inspected by a system that includes a vision assembly. The vision assembly includes an area light, a line generator, a sensor, and an image processor. The area light illuminates an area of the course material. The line generator generates a line of illumination across the area. The sensor captures an image of the area. The image processor analyzes the image. The image processor is configured to identify debris on the course material in response to the area light being activated and the image processor is configured to identify placement aberrations in response to the line generator being activated.

23 Claims, 7 Drawing Sheets

VISION INSPECTION SYSTEM DEVICE AND METHOD

CROSS REFERENCE TO RELATED APPLICATIONS

This application is a Continuation-in-Part of and claims priority to U.S. patent application Ser. No. 11/390,244, filed on Mar. 28, 2006, titled "VISION INSPECTION SYSTEM DEVICE AND METHOD," issued as U.S. Pat. No. 7,362,437 on Apr. 22, 2008, the disclosure of which is incorporated herein by reference in its entirety.

FIELD OF THE INVENTION

The present invention generally relates to a machine vision inspection device. More particularly, the present invention pertains to a machine vision inspection device for use with a composite material placement system.

BACKGROUND OF THE INVENTION

Composite items are generally constructed from layers of material that are laminated together. These layers are often referred to as partial or full plies. For structures exceeding the available material width, each layer is typically made up of a series of strips or courses of material placed edge to edge next to each other or are overlapped to some extent. Each ply may be in the form of woven fibers in a fabric, unidirectional fiber material, metal foils, adhesive films or a variety of other conformations. Unidirectional fiber material is often termed, "tape." The fibers may be made from any of a multitude of natural and/or "man-made" materials such as fiberglass, graphite, Kevlar®, and the like.

The courses are generally laid upon the form or tool in a specific pattern. Deviations from this pattern may result in unacceptable wrinkles, twist, gaps and/or overlap of the courses. Other errors that may occur during ply placement include foreign objects, such as, bits of backing material or debris ("blobs") becoming stuck to the surface of the tool or course. Blobs generally include bits of resin and stray fibers pulled from the tape that may ball up into "fuzz balls" or fiber wads.

In these and other instances, if the error is not identified and corrected prior to placement of the next ply, material properties of the completed composite item may be adversely affected. Conventionally, technicians have been employed to inspect the courses. This typically involves stopping course placement while the inspection occurs to insure thorough inspection and minimize risk to the technicians. Accordingly, inspection greatly increases the fabrication time and expense of the composite item. In an attempt to assist the inspection technicians, conventional machine vision systems have been utilized in the inspection process. However, these conventional machine vision systems are not capable of identifying all of the various types of anomalies. Nor are they capable of inspecting at the laydown rates currently achievable with multi-head tape lamination machines.

Accordingly, it is desirable to provide a method and apparatus capable of overcoming the disadvantages described herein at least to some extent.

SUMMARY OF THE INVENTION

The foregoing needs are met, to a great extent, by the present invention, wherein in one respect an apparatus and method is provided that in some embodiments identifies errors on placed plies.

An embodiment of the present invention relates to a system to inspect a course material applied to a substrate during fabrication of a composite item. The system includes a vision assembly that includes an area light, a line generator, a sensor, and an image processor. The area light illuminates an area of the course material. The line generator generates a line of illumination across the area. The sensor captures an image of the area. The image processor analyzes the image. The image processor is configured to identify debris on the course material in response to the area light being activated and the image processor is configured to identify placement aberrations in response to the line generator being activated.

Another embodiment of the present invention pertains to an apparatus for inspecting a course material applied to a substrate during fabrication of a composite item. The apparatus includes a means for diffusely illuminating an area of the course material, a means for generating a line of illumination across the area, means for capturing an image of the area, and a means for analyzing the image. The image is analyzed to identify debris on the course material in response to diffusely illuminating the area and the image is analyzed to identify placement aberrations in response to the line of illumination.

Yet another embodiment of the present invention relates to a method of inspecting a course material applied to a substrate during fabrication of a composite item. In this method, an area of the course material is diffusely illuminated, a line of illumination is generated across the area, an image of the area is captured, and the image is analyzed. The image is analyzed to identify debris on the course material in response to diffusely illuminating the area and the image is analyzed to identify placement aberrations in response to the line of illumination.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT

The present invention provides, in some embodiments, an in-process, machine vision, inspection system for a composite placement device and a method of using this system. In various embodiments, the system is suitable for use with an automated lamination device such as, for example, an automated fiber placement (AFP) machine, flat tape lamination machine (FTLM), numerically controlled (NC) contoured tape lamination machine (CTLM), multi-head tape lamination machine (MHTLM), and the like. These automated lamination devices generally include at least one placement head or "head" to place plies of composite material upon a mandrel, layup mold or tool to fabricate a composite item. The MHTLM may include a plurality of such heads. In an embodiment, the system includes a machine vision inspection assembly associated with each dispensing head of the MHTLM.

Figure 1:
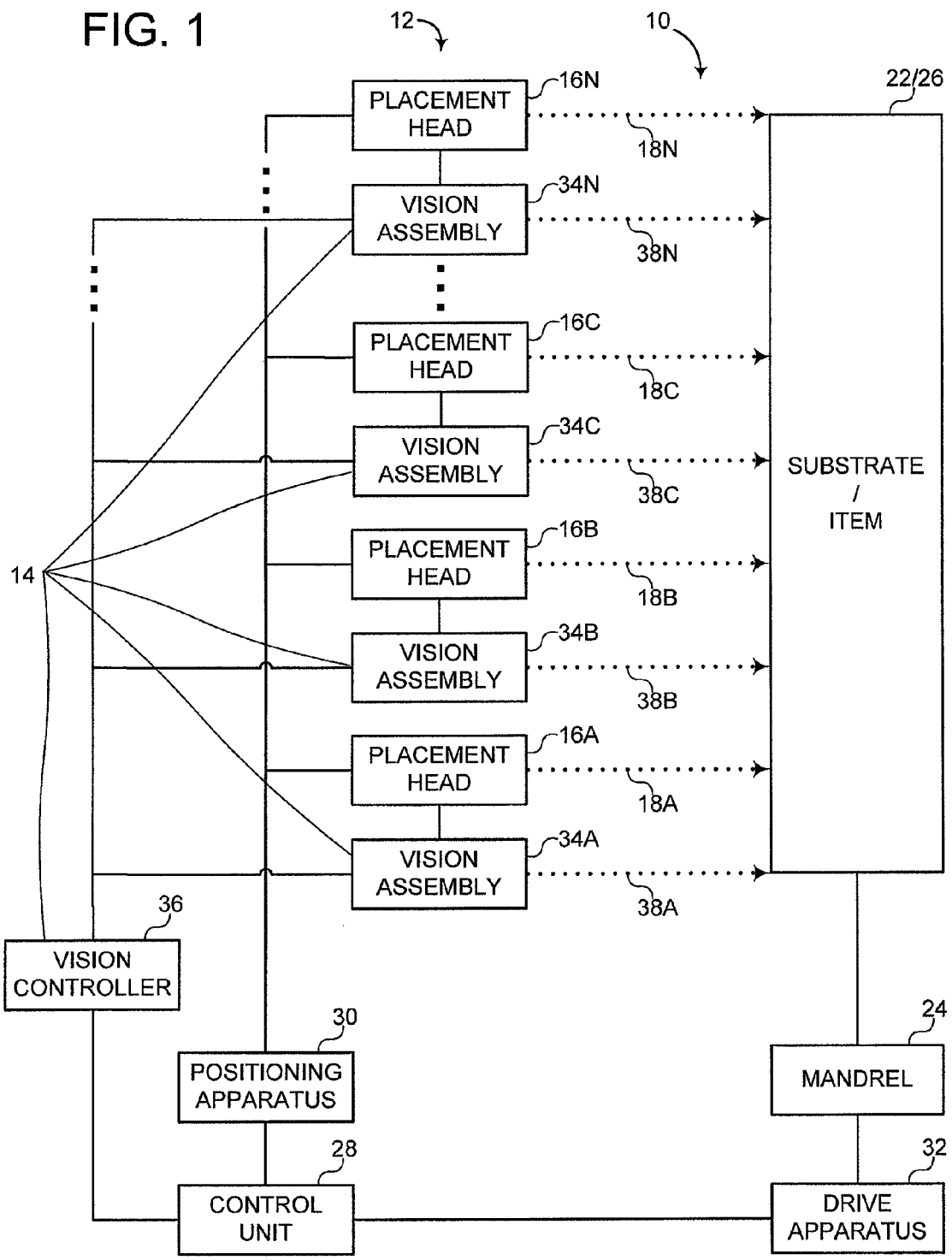
FIG. 1 is a block diagram of a multi-head tape lamination system according to an embodiment of the invention.

The invention will now be described with reference to the drawing figures, in which like reference numerals refer to like parts throughout. As shown in FIG. 1, a multi-head tape lamination system ("MHTLS") 10 suitable for use in an embodiment of the invention includes a multi-head tape lamination machine ("MHTLM") 12 and a machine-vision inspection system ("MVIS") 14. The MHTLM 12 includes one or more heads 16a-16n to place 18 a course 20 (shown in FIG. 2) upon a substrate 22. This substrate 22 includes a surface of a mandrel 24 and/or any previously placed courses 20. By placing courses 20 on the substrate 22 in this manner, an item 26 is generated. In addition, the MHTLM 12 includes a controller 28 to control a positioning device 30 and/or a drive apparatus 32. In addition, the controller 28 is configured to determine a relative position of the one or more heads 16a-16n on the mandrel 24 based upon positioning signals from the positioning device 30 and/or the drive apparatus 32. In an embodiment, the controller 28 is configured to receive a query signal in response to a detected flaw and return a position corresponding to the flaw. The positioning device 30 positions the heads 16a-16n relative to the substrate 22. The drive apparatus 32 positions or rotates the mandrel 24 upon which the substrate 22 is affixed.

The MVIS 14 includes at least one vision assembly 34a-34n and a vision controller 36. In an embodiment, each of the heads 16a-16n includes a respective vision assembly 34a-34n. As described herein, the vision assemblies 34a-34n are configured to inspect 38 the placed 18 courses 20.

Figure 2:
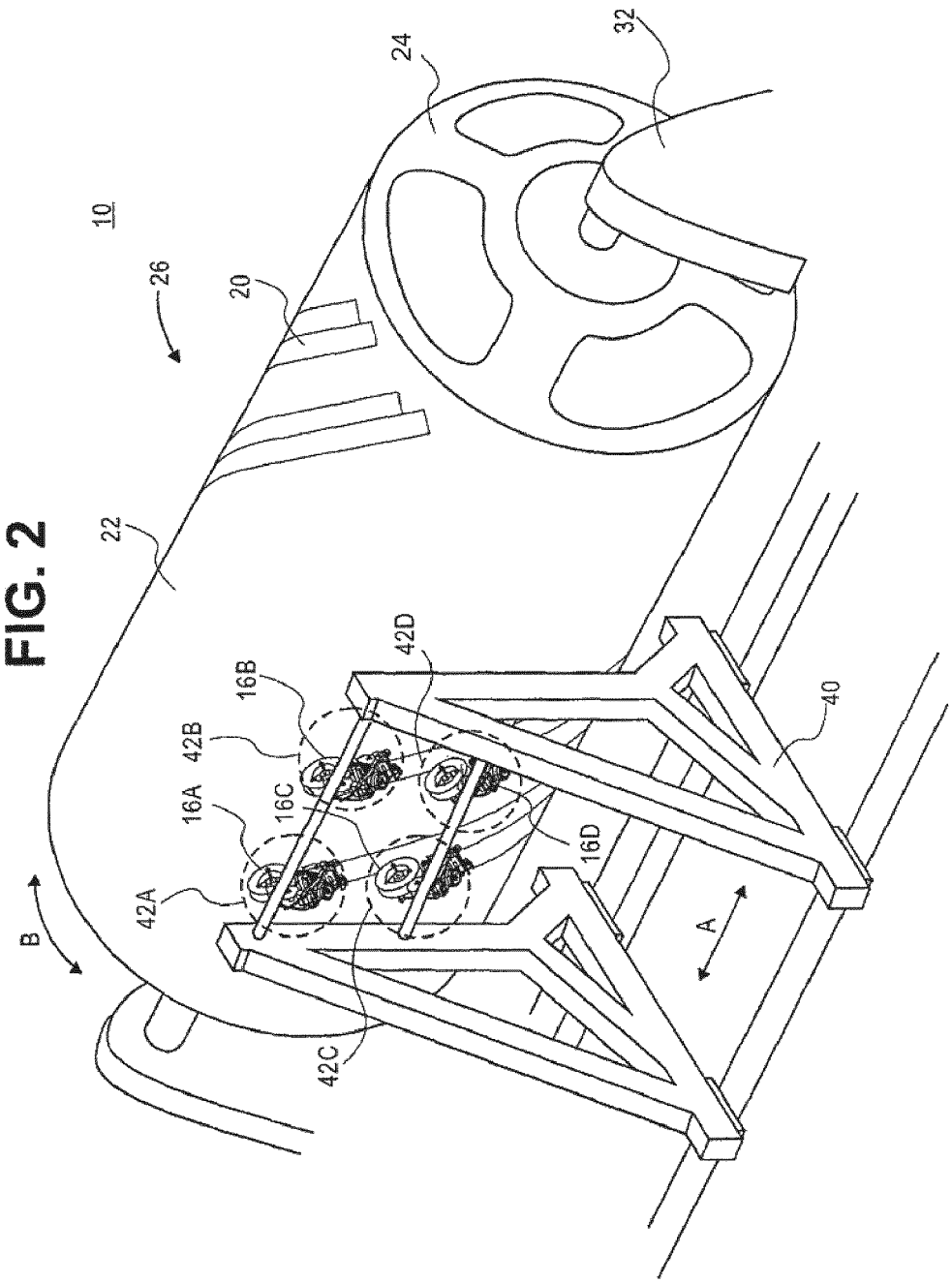
FIG. 2 is a perspective view of the multi-head tape lamination system according to an embodiment of the invention.

FIG. 2 is a perspective view of the MHTLM 12 according to an embodiment of the invention. As shown in FIG. 2, the MHTLM 12 includes a frame 40 to position the placement heads 16a-16d relative to the substrate 22. The frame 40 and substrate 22 are configured to move in directions A and B relative to one another. In this manner, some or all of the placements heads 16a-16d are configured to place respective courses 20 or strips of a composite tape upon the substrate 22. Each course 20 includes any suitable material to fabricate the item 26. Examples of suitable materials include metal foils, films, fibers, and the like. These materials may be coated or impregnated with resin. In a particular example, the course 20 includes carbon fibers that are pre-impregnated with a thermoset resin (pre-preg). In another example, the course 20 includes a titanium foil that is coated with a resin. The composite item 26 includes any suitable item or part that may be fabricated with the course 20. Particular examples include wing and fuselage components for an aircraft. Other examples include car and truck body and framing members and various other consumer products.

Increasing the number of heads 16a-16n employed in the fabrication of the item 26 increases the fabrication rate. Thus, by increasing the number of heads 16a-16n, the item 26 may be produced in less time and/or more economically. However, during placement of the courses 20, the head 16a is operable to pivot about any suitable number of axes. For example, the head 16a may pivot about 1 to 6 or more axes depending upon the shape of the item 26 being fabricated. As such, if too many heads 16a-16n are placed upon the frame 40, the heads 16a-16n may interfere with one another. In this regard, the MHTLS 10 includes a respective operational envelope 42a-42n for each head 16a-16n. For the sake of simplicity, the operational envelope 42a will be described herein and it is to be understood that the operational envelopes 42b-42n are of a similar nature. The operation envelope 42a defines a volume within which the head 16a operates. The operational envelope 42a is configured to avoid interference between the head 16a and any structure in the proximity of the head 16a. These structures include the frame 40, heads 16b-16n, substrate 22, and the like. For example, by disposing the heads 16a-16n such that the respective operational envelopes 42a-42n do not overlap, interactions between the heads 16a-16n, such as "head crashes," are minimized. It is an advantage of an embodiment of the invention that, the vision assembly 34a fits within the operational envelope 42a.

Of note, although four heads 16a-16d are depicted in FIG. 2, the various embodiments of the MHTLS 10 may include any suitable number of heads 16a-16n. For Example, 2, 4, 8, 16, and 32 or more heads 16a-16n are suitable for use with the MHTLS 10. In addition, heads 16a-16n may be added or removed as indicated to fabricated the item 26. In this regard, it is an advantage of an embodiment of the invention that, because a respective vision assembly 34a-34n is associated with each head 16a-16n, as the heads 16a-16n are added or removed, the associated vision assembly 34a-34n is added or removed as well.

Figure 3:
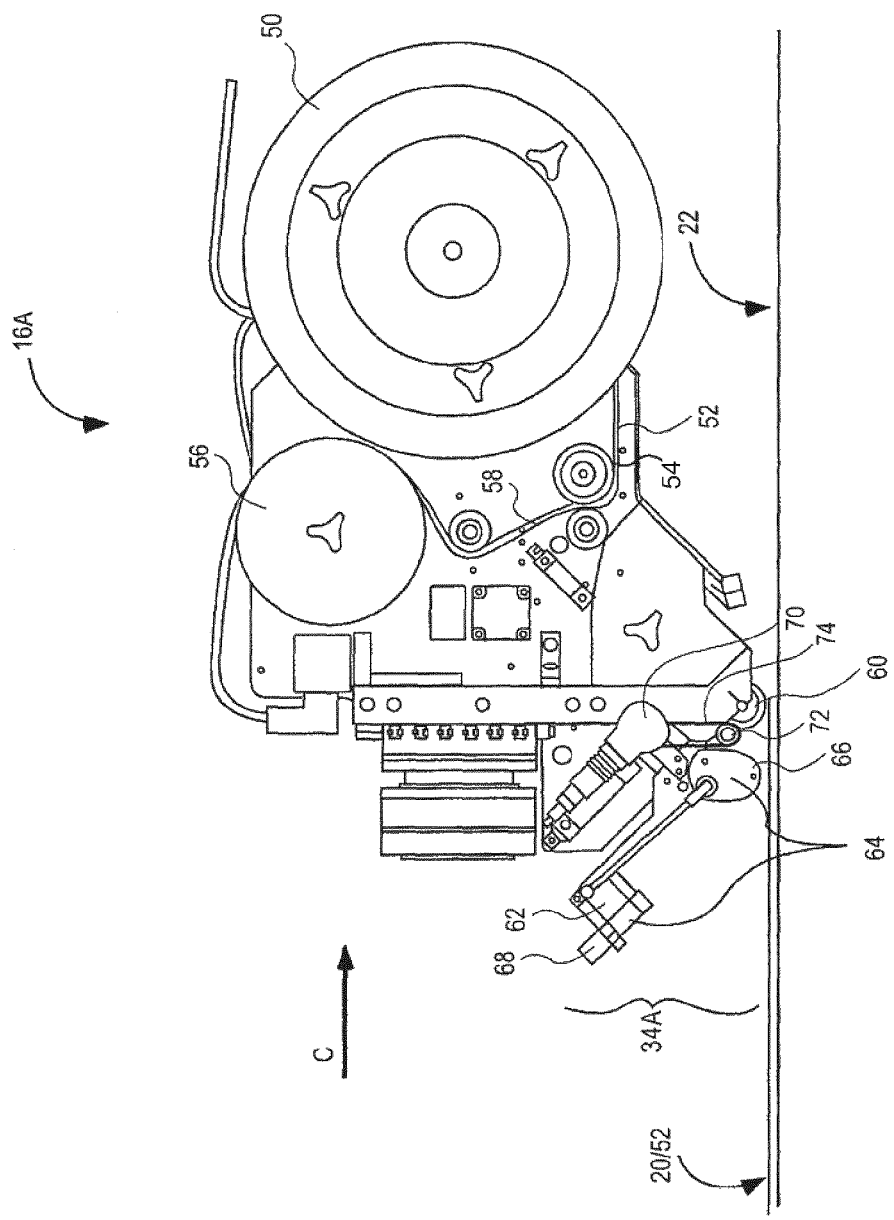
FIG. 3 is a side view of a head and vision assembly suitable for use with the multi-head tape lamination system of FIG. 1.

FIG. 3 is a side view of the head 16a and vision assembly 34a suitable for use with the MHTLS 10 of FIG. 1. As shown in FIG. 3, the head 16a includes a supply reel 50 to supply a tape 52. The tape 52 is threaded along a tape path 54. The head 16a further includes a take-up reel 56 to retain an option backing 58 that may be removed from the tape 52. The head 16a further includes a compaction roller 60 to compact or consolidate the tape 52 upon the substrate 22 (shown in FIG. 2). As shown in FIG. 3, the head 16a includes the vision assembly 34a. The vision assembly 34a includes a sensor 62 and lighting system 64. In an embodiment, the lighting system 64 includes one or more area lights 66 and a laser 68. In general, the area lights 66 illuminate a generalized area and may facilitate sensing foreign objects on the course 20. The laser 68 generates a line of illumination across the course 20 and may facilitate sensing misalignments, overlaps, gaps, and the like in course placement. The vision assembly 34a optionally includes an encoder 70, encoder drive 72, and belt 74.

In operation, the head 16a is guided in direction "C" along a path via the various movements of the frame 40 and the mandrel 24 and is configured to place the tape 52 upon the substrate 22. The tape 52 and the substrate 22 are configured to adhere to one another. For example, the tape 52 and/or the substrate 22 may be tacky. The compaction roller 60 is configured to press or urge the tape 52 towards the substrate 22 so as to consolidate the tape 52 into the layup. The vision assembly 34a is configured to sense this placed tape 52, the position of the placed tape relative to any adjacent tape 52 (e.g., a previously applied course 20 and the like), and/or any foreign object that may be present on the surface of the tape 52.

The encoder 70, if present, is configured to sense movement of the compaction roller 60 and/or the head 16a and output a signal in response to the sensed movement. In a particular example, the encoder drive 72 may mate with or engage the compaction roller 60 so as to move in response to movement of the compaction roller 60. The belt 74 is configured to translate movement of the encoder drive 72 to the encoder 70. In other examples, the encoder 70 may directly engage the encoder drive 72 and/or compaction roller 60 or the encoder 70 may be linked to the encoder drive 72 via a shaft or other such linking mechanism. If not present, the actions of the encoder 70, encoder drive 72, and belt 74 may be subsumed by a processor, such as the controller 28, that may be configured to generate signals in response to movement instruction or sensed movements performed by the MHTLS 10.

Figure 4:
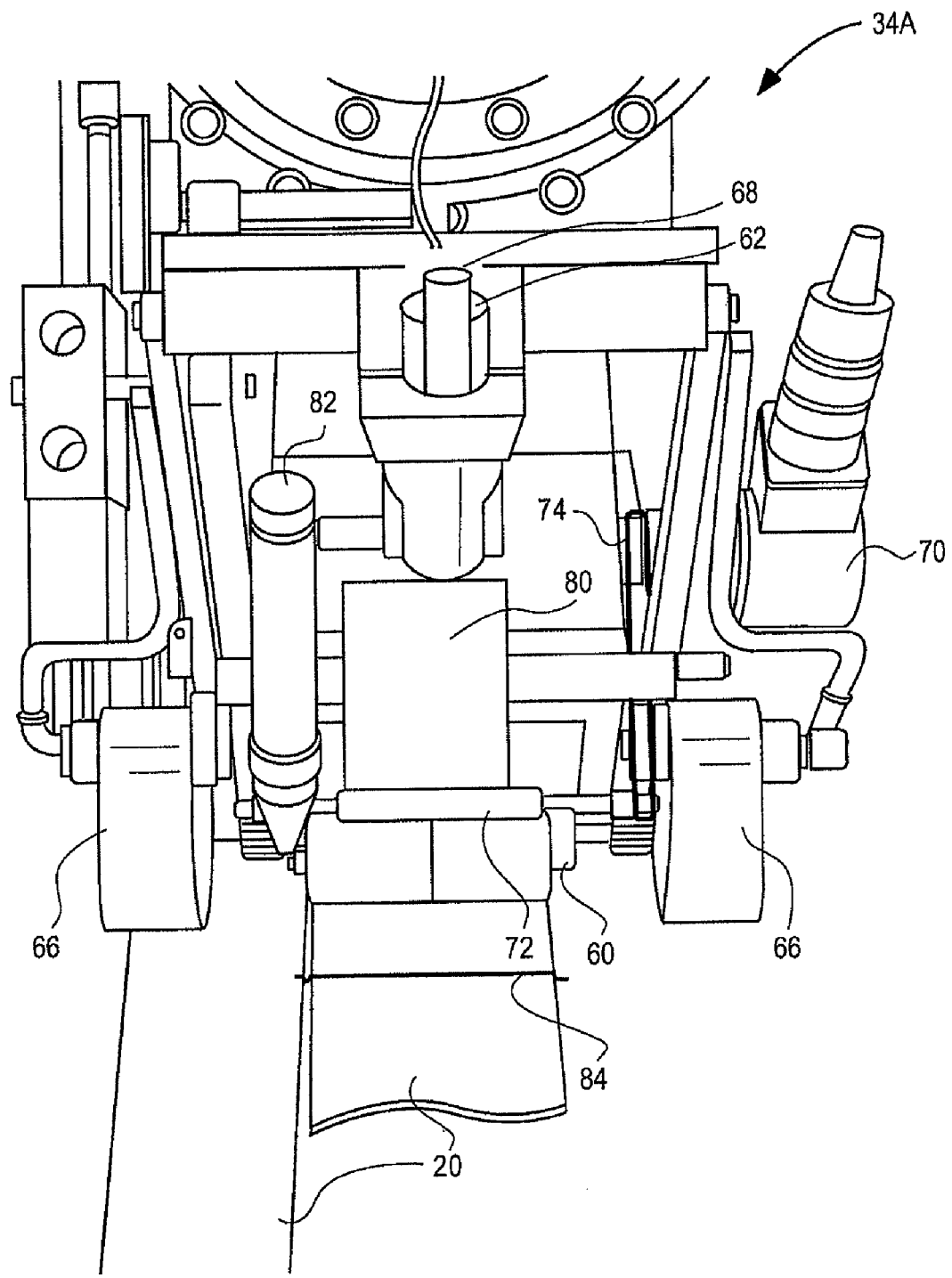
FIG. 4 is a rear view of the vision assembly and head suitable for use with the multi-head tape lamination system of FIG. 1.

FIG. 4 is a rear view of the vision assembly 34a and head 16a suitable for use with the MHTLS 10 of FIG. 1. As shown in FIG. 4, the vision assembly 34 optionally includes a mirror 80 and a marker 82. If included, the mirror 80 is configured to reflect or redirect light, or other such forms of electromagnetic radiation, towards the sensor 62. In this manner, illumination from the lighting system 64 may be configured to strike the course 20 at a relatively low angle and the sensor 62 may be configured to view the course 20 from a relatively higher angle. The relatively low incident angle of the lighting system 64 facilitates a variety of advantages. For example, having the area lights 66 disposed relatively near the course 20 and/or casting light substantially across the course 20 facilitates casting a longer shadow in response to striking a foreign object present on the course 20. In another example, the laser 68 may be disposed at a relatively low incident angle and configured to generate a line 84, or a plurality of lines 84, across the course 20. In this manner, relatively small deviations in the height of the course 20 generate relatively large deviations in the line 84 when viewed or sensed from a relatively high incident angle. For this reason, the mirror 80 may be disposed to redirect light from this relatively high incident angle towards the sensor 62. In other instances, the sensor 62 may be disposed to directly view the course 20 from a relatively higher angle and the mirror 80 and/or other reflective surface or redirecting device may be omitted.

The marker 82, if present, is configured to place or deposit an indicator upon the course 20. In an embodiment, the indicator is placed in response to a sensed flaw. For example, in response to sensing that a foreign object is present on the course 20, the marker 82 may be controlled to deposit the indicator on or near the foreign object. In this regard, the marker 82 may include any suitable marking device for generating an indicator upon the course 20. Examples of marking devices include ink or paint sprayers, pens, and the like.

Figure 5:
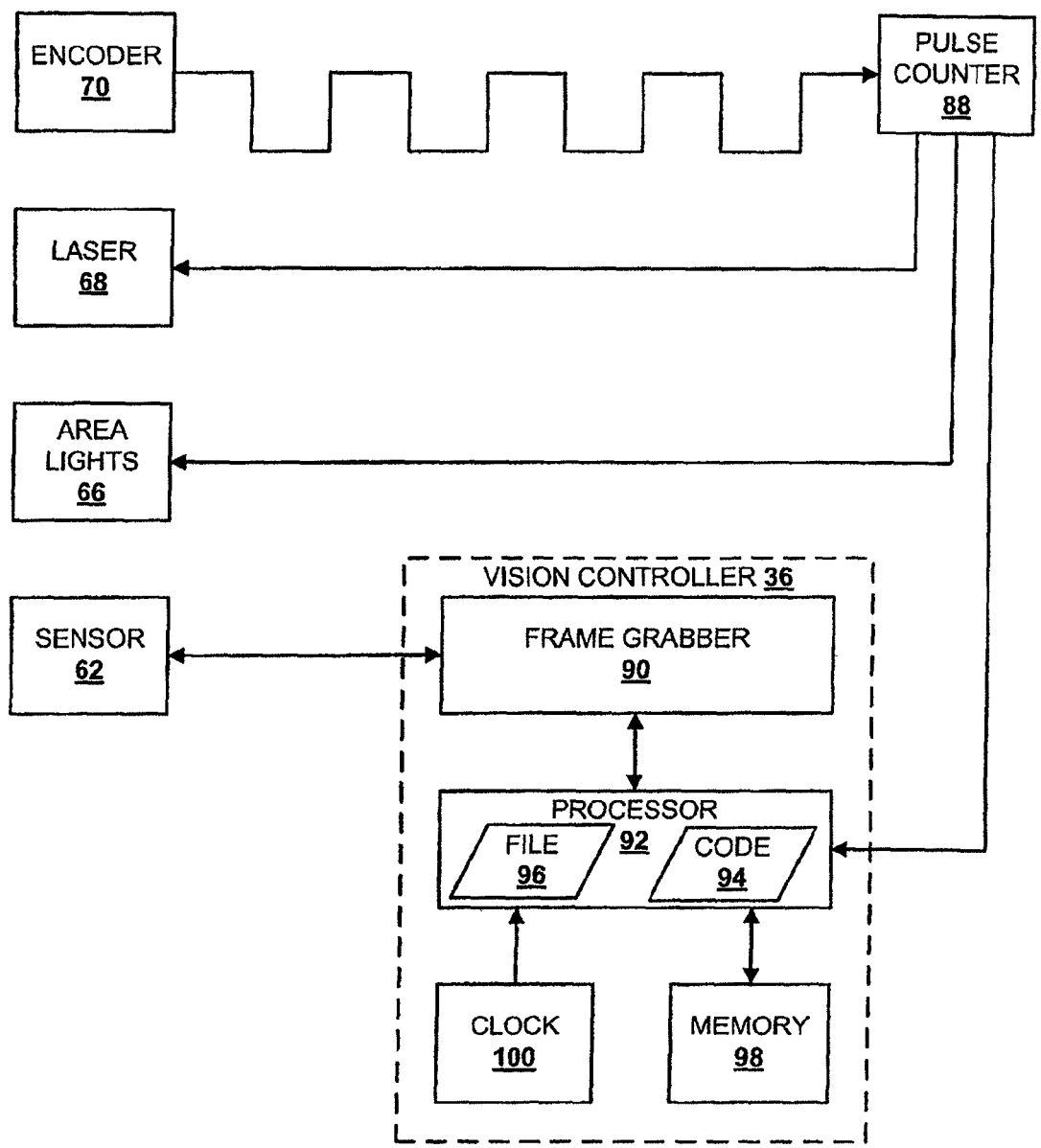
FIG. 5 is a block diagram of a vision controller suitable for use with the multi-head tape lamination system of FIG. 1.

FIG. 5 is a block diagram of the vision controller 36 suitable for use with the MHTLS 10 of FIG. 1. As shown in FIG. 5, the vision controller 36 is configured to receive signals from a pulse counter 88. The pulse counter 88 generally acts as a switch to control the lighting system 64. The pulse counter 88 is configured to receive signals corresponding to movement or rate of movement. In a particular example, the pulse counter 88 is configured to receive signals from the encoder 70 in response to movement of the compaction roller 60. In this example, as the rate of movement or rotation of the compaction roller 60 changes, the signals received by the pulse counter 88 are modified accordingly. In response, the pulse counter 88 is configured to generate signals to control the area lights, laser 68, and/or a frame grabber 90. For example, the pulse counter 88 is configured to control the area lights 66 and the laser 68 to turn on and illuminate the course 20 or to turn off. In various embodiments, the area lights 66 and the laser 68 may be controlled to turn on and off in an alternating fashion, to turn on and off simultaneously, to turn on and off independently, or to turn on essentially while the course 20 is being placed.

The vision controller 36 may include a processor 92, code 94, file 96, memory 98, clock 100, and the like. The processor 92 is configured to execute computer readable code such as the code 94. According to the code 94, the processor 92 is configured to receive signals from the pulse counter 88, forward and receive signals to and from the frame grabber 90, process images received from the frame grabber 90, store and retrieve information to and from the file 96 and memory 98, receive time signals from the clock 100 and the like. The file 96 is configured to store one or more of the following: positional information; time stamps; error codes; and the like.

Figure 6:
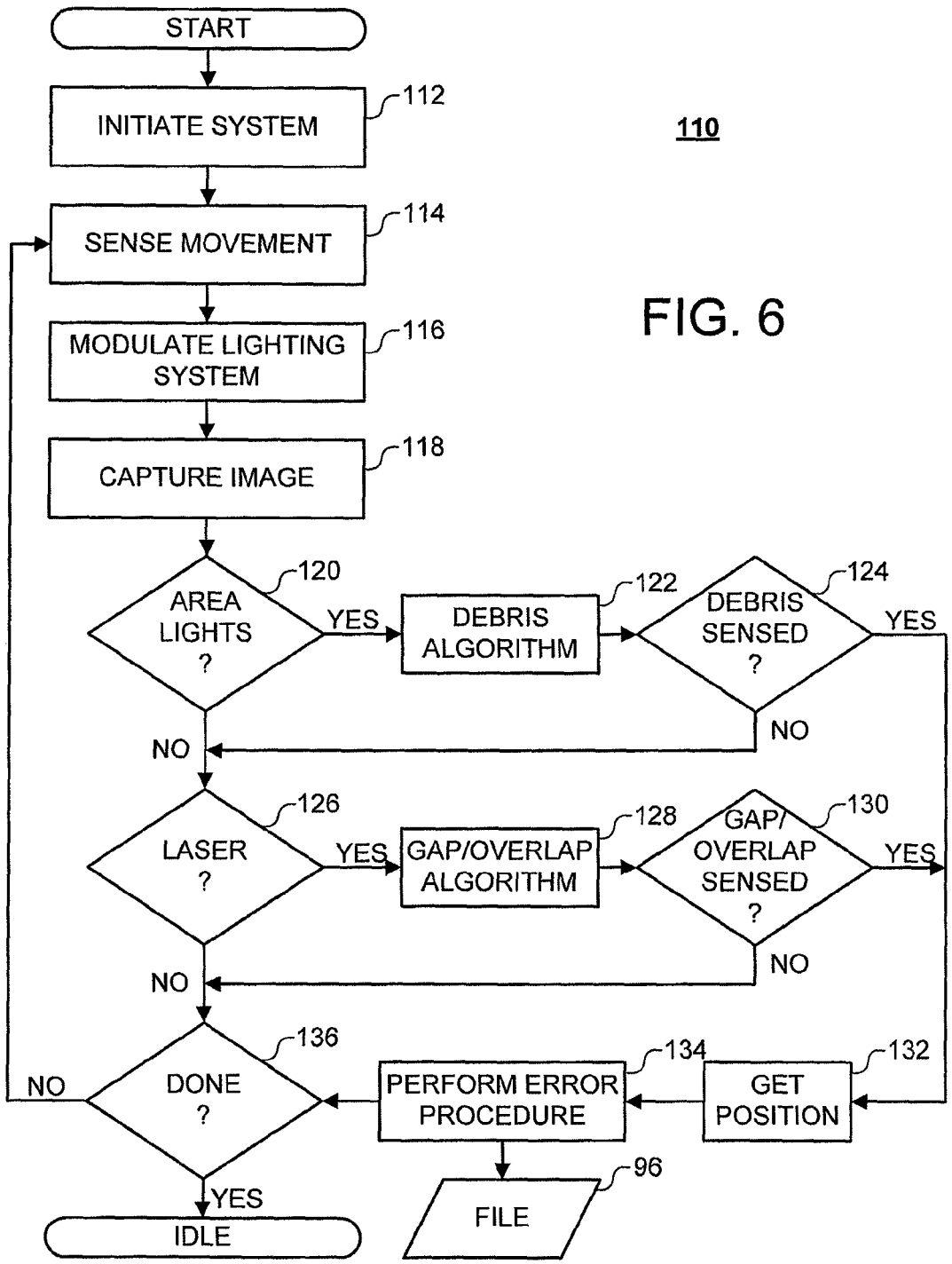
FIG. 6 is a flow diagram illustrating steps of a method in accordance with an embodiment of the invention.

FIG. 6 illustrates steps involved in a method 110 of inspecting the courses 20 placed on the substrate 22. Prior to the initiation of the method 110, a composite product, such as the item 26, is designed and, based on this design, a series of computer readable instructions specifying attributes of the composite product is generated. In addition, the MHTLS 10 is prepared for operation. These preparations may include, for example, generating the mandrel 24 based on the item 26, installing the supply reels 50, threading the tape 52 along the tape path 54, powering the MHTLS 10, calibrating the various systems, and the like.

At step 112, the MHTLS 10 is initiated. For example, the controller 28 may control the positioning device 30 and drive apparatus 32 to move relative to one another. In this manner, the heads 16a-16n may be controlled to engage and proceed along the substrate 22.

At step 114, movement may be sensed. For example, movement of the compaction roller 60 may be sensed and utilized at an indicator that the course 20 is being applied to the substrate 22. In particular, the encoder drive 72 may be rotated as a result of contact with the compaction roller 60, the rotation of the encoder drive 72 may, in turn, cause the belt 74 to rotate, and the rotation of the belt 74 may modulate the encoder 70. In response to modulation, the encoder 70 may forward a signal to the pulse counter 88 and/or a controller such as the vision controller 36. For example, the encoder 70 may generate a signal or pulse in response to a predetermined increment of the tape 52 being placed upon the substrate 22. The predetermined increment may include any suitable value such as, 1 inch (25.4 mm), 0.1 inch (2.54 mm), 0.01 inch (0.254 mm), 0.001 inch (0.0254 mm), and the like.

It is an advantage of an embodiment that the MVIS 14 dynamically responds to changes in laydown rates. For example, in response to the head 16a placing the tape 52 at a faster rate, the encoder 70 may be induced to generate signals at a similarly faster rate. As described herein, in this manner, the MVIS 14 is operable to dynamically modulate the frequency of inspection.

In another embodiment, movement instructions for the mandrel 24 and/or the positioning device 30 may be utilized to sense or determine that movement has occurred or the tape 52 has been dispensed.

At step 116, the lighting system 64 may be modulated. In an embodiment, the lighting system 64 may be alternated between the area lights 66 and the laser 68. That is, either the area lights 66 or the laser 68 is activated and, in response to a predetermined number of signals or pulses, the other is activated. For example, in response to receiving signals from the encoder 70, the pulse counter 88 or the vision controller 36 may be configured to turn off whichever of the area lights 66 and laser 68 is on and turn on whichever of the area lights 66 and laser 68 is off. This alternating activation may be continued for the duration of the laydown process.

At step 118, an image is captured. For example, the frame grabber 90 is controlled to obtain the image or frame from the sensor 62. In various embodiments, the frame grabber 90 is controlled to capture the image in response to signals from the processor 92 and/or the pulse counter 88. Thereafter, the captured image may be forwarded to the processor 92 for image processing.

At step 120, it may be determined whether the area lights 66 are activated. For example, signals forwarded via the pulse counter 88 may include a code or indicator that indicates which of the area lights 66 and the laser 68 is activated. In another example, image analysis algorithms may be configured to determine which of the area lights 66 and the laser 68 is activated in response to differing lighting conditions. In response to determining that the area lights 66 are activated, a debris algorithm is performed at step 122. In response to determining that the area lights 66 are not activated, it is determined if the laser 68 is activated at step 126.

At step 122, the debris algorithm is performed. For example, the captured image may be forwarded to the processor 92 and, according to the code 94, the captured image may be suitably manipulated and/or analyzed. Suitable examples of manipulations and/or analysis include: modulating the contrast of the image to emphasize light and/or dark regions; identifying light and/or dark regions; comparing any identified light and/or dark regions to a predetermined threshold or set of high and/or low values; and the like.

At step 124, it may be determined whether debris is present on the course 20. For example, if an identified light region is determined to exceed a predetermined threshold, it may be determined that debris is present on the course 20. In response to determining that debris is present on the course 20, an error procedure is performed at step 134. In response to determining that debris is not present on the course 20, it may be determined if the laser 68 is activated at step 126.

At step 126, it may be determined whether the laser 68 is activated. For example, signals forwarded via the pulse counter 88 may include a code or indicator that indicates which of the area lights 66 and the laser 68 is activated. In another example, image analysis algorithms may be configured to determine which of the area lights 66 and the laser 68 is activated in response to differing lighting conditions. In response to determining that the laser 68 is activated, a gap/overlap algorithm may be performed at step 130. In response to determining that the laser 68 is not activated, it is determined if the method 110 is completed at step 136.

At step 128, the gap/overlap algorithm is performed. For example, the captured image may be forwarded to the processor 92 and, according to the code 94, the captured image may be suitably manipulated and/or analyzed. Suitable examples of manipulations and/or analysis include: identifying one or more of the lines 84; identifying aberrations in the identified line(s) 84 such as discontinuity, convergence, divergence, skew, and the like; comparing any identified aberrations to a predetermined threshold or set of high and/or low values; and the like.

At step 130, it may be determined whether gaps and/or overlaps are present on the course 20. For example, if an identified aberration is determined to exceed a predetermined threshold, it may be determined that a gap and/or overlap is present on the course 20. In response to determining that a gap and/or overlap is present on the course 20, the error procedure is performed at step 134. In response to determining that a gap and/or overlap is not present on the course 20, it may be determined if the method 110 is completed at step 136.

At step 132, positional information corresponding to the detected flaw may be obtained. For example, the controller 28 may be queried for the positional data associated with the detected flaw. The controller 28 is configured to determine a relative position of the one or more heads 16a-16n on the mandrel 24 based upon positioning signals from the positioning device 30 and/or the drive apparatus 32. In an embodiment, the controller 28 is configured to receive a query signal in response to a detected flaw and return a position corresponding to the flaw.

At step 134, the error procedure may be performed. For example, any identified debris, gap, and/or overlap may be logged and stored to the file 96. In addition or alternatively, information related to the identified debris, gap, and/or overlap may be forwarded to another component of the MHTLS 10 and/or an operator for logging and/or corrective actions. In a particular example, the information related to the identified debris, gap, and/or overlap may include: time/date stamp; ply number; segment number; head number; course number; master axis position; block number; event identifier number; frame number; positional information; and the like.

At step 136, it may be determined whether the method 110 is completed. For example, if the layup for the item 26 is determined to be complete and/or the MHTLS 10 is deactivated, it may be determined that the method 110 is completed and the MVIS 14 may idle or shutdown as appropriate. If it is determined that the method 110 is not complete, movement may be sensed at step 114.

Figure 7:
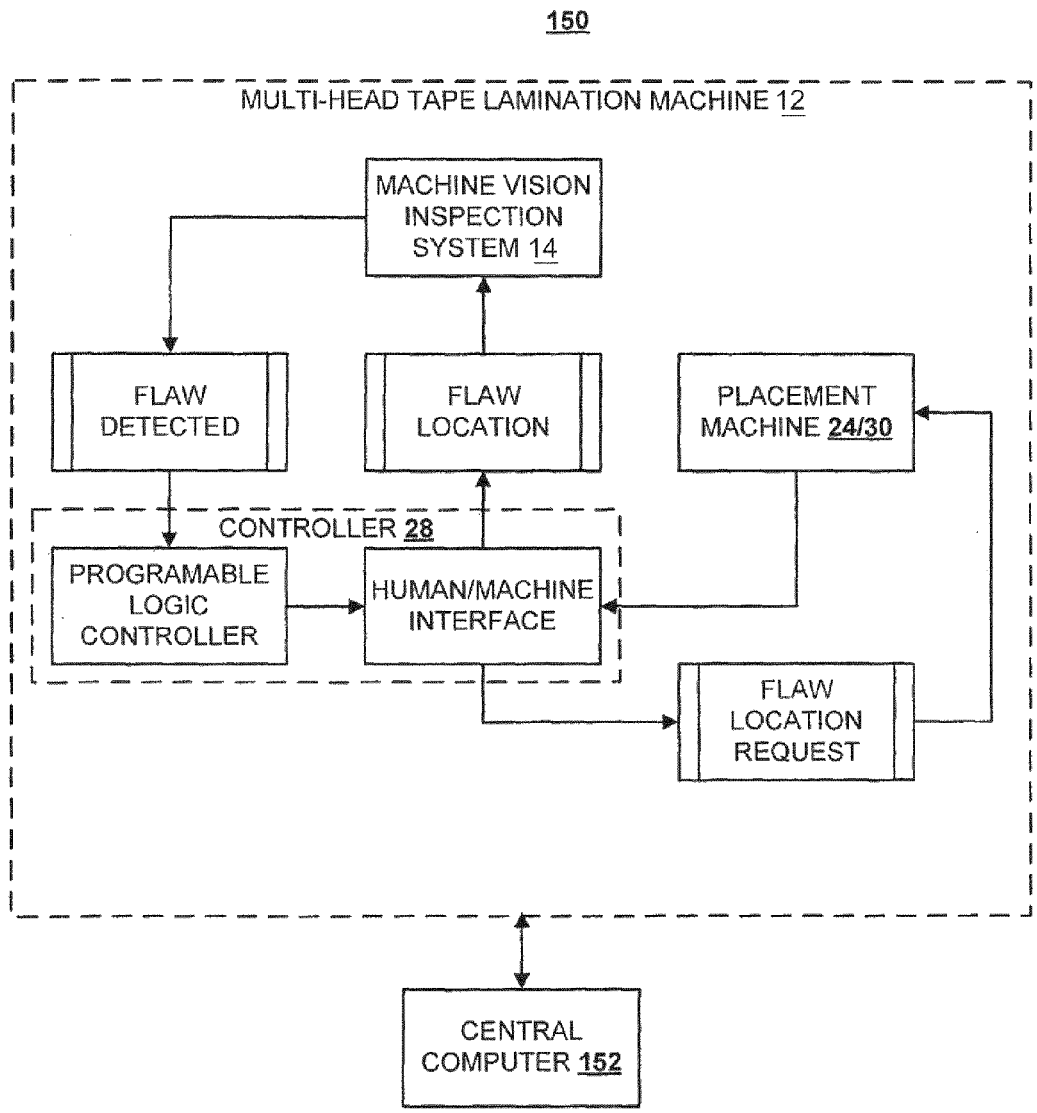
FIG. 7 is a block diagram for a communication architecture suitable for use an embodiment of the invention.

FIG. 7 is a block diagram for a communication architecture 150 suitable for use an embodiment of the invention. As shown in FIG. 7, in response to the detection of a flaw, the controller 28 may query positioning apparatus and/or mandrel 24 to obtain a flaw location. The flaw location may be stored to a defect logging computer such as, for example, a central computer 152. In addition, other with information related to the detected flaw may be stored to the central computer 152. Specific examples of other with information related to the detected flaw may include one or more of: time/date stamp; ply number; segment number; head number; course number; master axis position; block number; event identifier number; frame number; positional information; and the like.

The many features and advantages of the invention are apparent from the detailed specification, and thus, it is intended by the appended claims to cover all such features and advantages of the invention that fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system to inspect a course material applied to a substrate during fabrication of a composite item, the system comprising:
   a vision assembly comprising:
      an area light to illuminate an area of the course material;

a line generator to generate a line of illumination across the area;

a sensor to capture an image of the area; and an image processor to detect a flaw, wherein the image processor is configured to identify debris on the course material in response to the area light being activated and the image processor is configured to identify placement aberrations in response to the line generator being activated; and a controller to query a positioning device in response to detection of the flaw, the controller obtaining a head position corresponding to the flaw based upon positioning signals from the positioning device.

2. The system according to claim 1, further comprising:
a switch to alternatively activate the area light and the line generator.

3. The system according to claim 2, wherein the switch varies a switching rate in response to a laydown rate.

4. The system according to claim 1, further comprising a plurality of heads and each of the plurality of heads is configured to place a respective strip of the course material on the substrate, wherein each of the plurality of heads comprises a respective vision assembly.

5. The system according to claim 1, further comprising:
a marker to mark the area in response to determining the area includes an error.

6. The system according to claim 1, wherein the area light is configured to illuminate the area at a relatively lower angle of incidence than the sensor.

7. The system according to claim 1, wherein the line generator is configured to generate the line on the area at a relatively lower angle of incidence than the sensor.

8. The system according to claim 1, wherein the line generator is a laser.

9. The system according to claim 8, wherein the laser is configured to generate a set of lines across the area.

10. The system according to claim 1, wherein placement aberrations include at least one of overlap and gaps.

11. The system according to claim 1, further comprising:
a mirror to redirect light from the area towards the sensor from a relatively higher angle of incidence than the line generator and the area light.

12. An apparatus for inspecting a course material applied to a substrate during fabrication of a composite item, the apparatus comprising:

means for diffusely illuminating an area of the course material;

means for generating a line of illumination across the area;

means for capturing an image of the area;

means for analyzing the image to detect a flaw, wherein the image is analyzed to identify debris on the course material in response to diffusely illuminating the area and the image is analyzed to identify placement aberrations in response to the line of illumination; and means for obtaining a head location corresponding to the flaw based upon positioning signals from a positioning means in response to detecting the flaw.

13. The apparatus according to claim 12, further comprising:
means for alternatively switching between the diffuse illumination and the line of illumination.

14. The apparatus according to claim 13, further comprising:
means for varying a switching rate in response to a laydown rate.

15. The apparatus according to claim 12, further comprising:
means for marking the area in response to determining the area includes an error.

16. The apparatus according to claim 12, further comprising:
means for illuminating the area at a relatively lower angle of incidence than the sensor.

17. The apparatus according to claim 12, further comprising:
means for generating a set of lines across the area.

18. A method of inspecting a course material applied to a substrate during fabrication of a composite item, the method comprising:

diffusely illuminating an area of the course material;

generating a line of illumination across the area;

capturing an image of the area; and analyzing the image to detect a flaw, wherein the image is analyzed to identify debris on the course material in response to diffusely illuminating the area and the image is analyzed to identify placement aberrations in response to the line of illumination;

querying a positioning device for a location corresponding to the flaw in response to detecting the flaw; and obtaining a head position corresponding to the flaw based upon positioning signals from the positioning device.

19. The method according to claim 18, further comprising:
alternatively switching between the diffuse illumination and the line of illumination.

20. The method according to claim 19, further comprising:
varying a switching rate in response to a laydown rate.

21. The method according to claim 18, further comprising:
marking the area in response to determining the area includes an error.

22. The method according to claim 18, further comprising:
illuminating the area at a relatively lower angle of incidence than the sensor.

23. The method according to claim 18, further comprising:
generating a set of lines across the area.

* * * * *